(12) United States Patent
Young

(10) Patent No.: US 6,464,494 B1
(45) Date of Patent: Oct. 15, 2002

(54) COMPOSITE ORTHODONTIC DEVICE

(76) Inventor: David V. Young, 445 E. 4500 South, #175, Murray, UT (US) 84107

( * ) Notice: Subject to any disclaimer, the term of this patent is extended or adjusted under 35 U.S.C. 154(b) by 0 days.

(21) Appl. No.: 09/627,872

(22) Filed: Jul. 28, 2000

(51) Int. Cl.[7] .................................................. A61C 3/00
(52) U.S. Cl. .......................................... 433/18; 433/24
(58) Field of Search .............................. 433/2, 6, 8, 18, 433/19, 24

(56) References Cited

U.S. PATENT DOCUMENTS

| | | | |
|---|---|---|---|
| 4,915,630 A | | 4/1990 | Honig .......................... 433/215 |
| 4,950,158 A | * | 8/1990 | Barngrover et al. ........... 433/11 |
| 5,011,403 A | * | 4/1991 | Sadoun et al. .................. 433/9 |
| 5,439,379 A | * | 8/1995 | Hansen ........................... 433/9 |
| 5,522,725 A | * | 6/1996 | Jordan et al. ................... 433/9 |
| 5,957,686 A | | 9/1999 | Anthony ....................... 433/19 |

OTHER PUBLICATIONS

Mayes, Bite Turbos . . . New Levels of Bite–Opening Acceleration, *Clinical Impressions*, vol. 6, No. 1, p. 15 (1997).
Aubrey, The Bite Fixer, *Clinical Impressions*, vol. 8, No. 2, p. 10 (1999).
Epstein, et al., Establishing the Posterior Occlusal Level with a Built–In Biteplate, *Clinical Impressions*, vol. 8, No. 3, p. 14 (1999).

* cited by examiner

*Primary Examiner*—Cary O'Connor
(74) *Attorney, Agent, or Firm*—Thorpe North & Western, LLP

(57) ABSTRACT

The present invention provides a composite orthodontic device including a base of a first material, with a first surface configured to facilitate attachment of the base to a tooth and a second surface configured to provide a mechanical interlock facilitating attachment of a bumper formed of a second material different from the first material.

75 Claims, 4 Drawing Sheets

COMPOSITE ORTHODONTIC DEVICE

THE FIELD OF THE INVENTION

The present invention relates generally to orthodontics. More specifically, the inventor relates to devices used in the field of orthodontics for a variety of orally-related disorders, such as bite disorders.

BACKGROUND OF THE INVENTION

Malocclusions, or bite disorders, present a variety of problems for those individuals who suffer from them. Headaches, jaw tightening and fatigue, irregular and accelerated tooth wear, inappropriate tooth height, disproportionate facial height, and difficulty in chewing and speaking, are few examples of specific problems which may be experienced.

Further, in orthodontic treatment, malocclusions may hinder or inhibit other facets of treatment, such as tooth straightening. For example, many malocclusions present a deep anterior over-bite, or under-bite pattern, which makes placement of orthodontic brackets on the incisors difficult or impossible. In such cases, bracket placement must be postponed until the bite has been corrected, as the deep bite causes the brackets to fall within the bite plane ("bite plane" as used herein is defined below). While in the bite plane, the brackets are at risk of becoming loosened or dislodged by undesirably coming in contact with the vertically opposing teeth. Further, the vertically opposing teeth may become traumatized by continuous contact with the brackets.

In order to correct a malocclusion, the muscles involved in biting and chewing must become "de-programmed" from incorrect biting habits. Opposing upper and lower teeth have a complimentary anatomy which is designed to maximize surface contact between them for efficient mastication. When opposing teeth are incorrectly positioned, a degree of lateral and anterial posterial, or horizontal movement, is required in order to close the teeth in the manner dictated by their ornamentation. Such lateral movement quickly becomes a subconscious habit in controlling the bite-facilitating muscles, such as the masseter muscle, which is not easily broken.

De-programming the biting muscles and determining the position of the "natural," or correct occlusion, requires the patients' bite to be opened so that the teeth no longer occlude in a manner determined by incorrectly placed teeth. In short, an occlusion which dictates lateral anterial posterial movements during the biting or chewing process must be eliminated for a period of time sufficient to allow the biting muscles to resume a natural, or correct, biting motion. It is often advantageous to engage such de-programming simultaneously with the alignment of the teeth into a correct position by discluding the bite.

While various devices have been employed to accomplish the afore-mentioned tasks, practitioners of the art have encountered problems in attempting to do so and provide the advantages of maximum patient compliance and comfort. Additionally, minimization of intrusiveness, tooth damage, and installation and removal efforts have proved difficult.

In view of the foregoing, it has been recognized by the inventor that a device for treating malocclusions which maximizes patient compliance with treatment is desirable. Further, a device for treating malocclusions which is minimally invasive, and provides a maximum level of patient comfort and remains hidden, or which is aesthetically pleasing is highly desirable. Additionally, a device for treating malocclusions which minimizes installment and removal effort is very desirable. Finally, it has been recognized that a device for treating malocclusions which minimizes the risk of damage to the teeth is extremely desirable.

SUMMARY OF THE INVENTION

Accordingly, the present invention provides a composite orthodontic device comprising a base made of a first material, having a first surface configured for facilitating attachment to a tooth, and a second surface configured to provide a mechanical interlock facilitating joining of a bumper formed of a second material different from said first material; and a bumper joined to said base, said bumper being configured for treating malocclusions.

In a more detailed aspect of the invention, the first material from which the base is made can be a metal. Metal suitable for use in an orthodontic device can be used, and by way of example without limitation, the metal can be stainless steel, titanium, titanium alloys, brass, gold, silver, and mixtures thereof.

In another detailed aspect of the invention, the second material, different from the first material, from which the bumper can be made a polymeric resin. Any of the polymeric resins suitable for use in such an orthodontic device can be used, and by way of example and without limitation, the polymeric resin can be acrylic resins, rubber, plastic, microfilled resins, macrofilled resins, unfilled resins, acrylic-metal composites, and mixtures thereof.

While the first surface of the base can have any configuration suitable for tooth attachment, in one aspect, the configuration can be a configuration which aids attachment to a tooth by providing a mechanical interlock to enhance bonding with an adhesive. For example, a rough surface or other non-planer or relieved surface can be used to provide a suitable mechanical interlock. Further examples of specific configurations include, but are not limited to, a multiplicity of cavities or ridges, as well as a surface comprising a mesh, such as a wire mesh.

Likewise, the configuration of the second surface can be a relieved or roughened surface, sufficient to facilitate joining of the bumper to the base. Specific examples of configurations which can be used include, but are not limited to, a plurality of cavities, ridges, or projections, such as bumps, hooks, and elongated rods. In many instances, a single projection can provide suitable support to accomplish the desired joining action. In one aspect of the present invention, the configuration of the second surface can comprise a mesh, such as a wire mesh.

In a further more detailed aspect, the base can be configured to allow convenience in removing or "de-bonding" the device of the present invention from a tooth surface to which it has been attached. In one aspect, the base can have an outer edge comprising a material thickness sufficient to facilitate engagement by a de-bonding instrument such as a ligature plier while the base is installed on a tooth. In another aspect, the base can have a width greater than a width of said bumper, and can wrap around an edge of the bumper, such that a greater portion of the base is exposed when the device is installed on a tooth, likewise facilitating access and purchase with a de-bonding instrument. In yet another aspect of the invention, the base can further comprise a crumple zone, or plurality of crumple zones, formed within said base; and adjacent and extending along an edge thereof.

Within known practical limitations, the bumper of the device can take any configuration which is suitable for accomplishing the desired task of opening the bite of a patient. However, in a more detailed aspect, the bumper can have a substantially planar tooth-contacting surface which is generally parallel to a bite plane in the mouth when the device is installed in the mouth. In another more detailed aspect, the planar tooth-contacting surface can have rounded edges.

When it is desirable to move teeth of either the mandible or maxilla in an anterior or posterior direction with respect to the other, the planar tooth-contacting surface can be formed at an angle which intersects a bite plane in the mouth when the device is installed in the mouth, and which tends to pull or push the contacting teeth in the desired direction.

A device in accordance with principles of the present invention can be used for multiple applications. For example, as described above, the device can be used in order to treat malocclusions. However, the device can also be used in a similar manner to treat a compulsive habit involving the oral cavity when the bumper is properly configured.

In one such more detailed aspect, such a device can comprise a bumper having a shape configured to provide a deterrent effect when physically contacted upon an outward surface.

Examples of deterrent configurations, without limitation, include shapes terminating in at least one sharp point, shapes terminating in at least one sharp ridge, and a bumper of a size which presents sufficient mass to discourage contact.

Principles of the present invention are also applicable to methods and processes relating to for treating a malocclusion, or a compulsive habit. Such a method can comprise the steps of: a) providing a device comprising: 1) a base made of a first material, having a first surface configured for facilitating attachment to a tooth, and a second surface configured to provide a mechanical interlock for facilitating attachment of a bumper formed of a second material different from said first material; and 2) a bumper joined to said base; and b) attaching said device to a surface of a tooth, so as to mitigate the malocclusion.

In a more detailed aspect, examples of compulsive habits include, but are not limited to, thumb and digit sucking and tongue thrusting. While the device can be attached to the surface of any tooth which provides a placement suitable to achieve a desired effect, in one aspect of the invention, the tooth is attached to an incisor, on either a lingual or facial surface.

In addition to methods of treating the above-mentioned conditions, in a more detailed aspect principles of the present invention encompass methods for attaching a bumper of a polymeric resin to a tooth, and for facilitating removal of a bumper of a polymeric resin from a tooth. In one aspect, a method for attaching a bumper of polymeric resin to a tooth comprises the steps of: providing a base made of a material different from said polymeric resin, having a first surface configured for facilitating attachment to the tooth, and a second surface configured to provide a mechanical interlock for facilitating attachment of the bumper formed of a polymeric resin; providing a bumper of polymeric resin; joining the bumper to the second surface of said base; and attaching the first surface of said base to a tooth.

In another detailed aspect of the invention, a method for facilitating removal of a bumper of polymeric resin from a tooth further comprises the steps of: providing a base made of a material different from said polymeric resin, having a configuration facilitating direct contacting of, and getting improved purchase on, the base with a de-bonding instrument when installed on a tooth; and joining the bumper to a said base. When such a composite device is bonded to a tooth, it is more easily de-bonded by the proper tool at the end of treatment.

There has thus been outlined, rather broadly, and in general terms, some of the more important features of the invention so that the detailed description thereof that follows can be better understood, and so that the present contribution to the art can be better appreciated. Other features and advantages of the present invention will become more clear from the following detailed description of the invention, taken with the accompanying drawings and appended claims.

DETAILED DESCRIPTION

Figure 1:
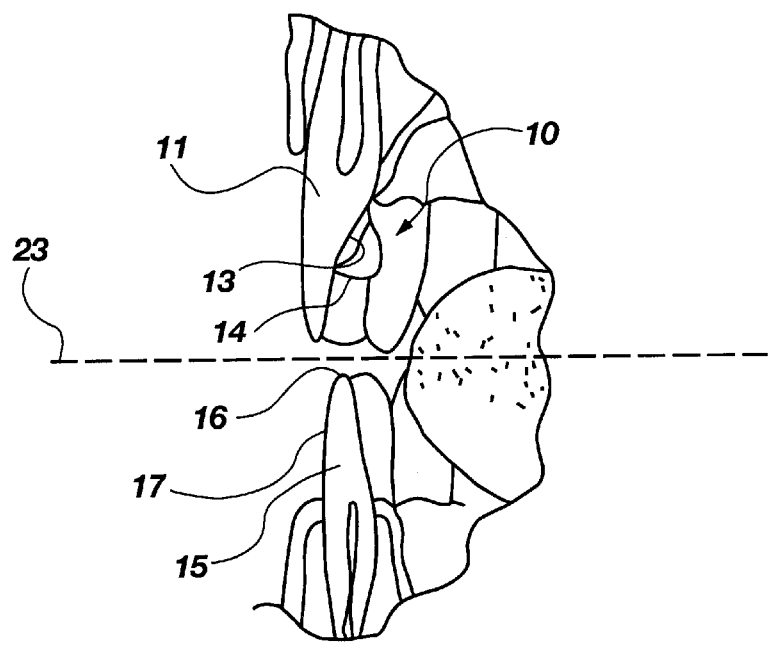
FIG. 1 is a cut-away cross-sectional view of a portion of a human mouth having an embodiment of a composite device in accordance with principles of the present invention mounted on the lingual surface of an upper incisor.

Before the present exemplary device(s) for treating malocclusions and other disorders is disclosed and described, it is to be understood that this invention is not limited to the particular design and materials disclosed herein, but is extended to equivalents thereof as will now and in the future be recognized by one of ordinary skill in the relevant art. It should also be understood that terminology employed herein is used for the purpose of describing particular embodiments only, and is not intended to be limiting.

It is noted that, as used in this specification and the appended claims, the singular forms "a" and "the" include plural referents, unless the context clearly dictates otherwise. Thus, as examples, reference to "a polymeric resin" includes reference to one or more of such polymeric resins, reference to "an occlusion" includes reference to one or more types of occlusions, such as type I, II, or III malocclusions, and reference to "a tooth" includes reference to one or more teeth.

In describing and claiming the present invention, the following terminology will be used in accordance with the definitions set forth below.

As used herein "bumper" refers to a portion of an orthodontic device, which functions in preventing occlusion of teeth, and/or placing a desired amount of distance between upper and lower teeth, by contacting a biting edge of a tooth which is vertically opposed to a tooth upon which the orthodontic device is installed. A bumper can take any shape desired or required to perform the particular task for which it is employed. For example, the bumper can be configured to be generally parallel to a bite plane as installed in the mouth, when no repositioning of the mandible or maxilla is desired. Additionally, when repositioning of the mandible or maxilla is desired, the bumper can be configured at an angle to obliquely intersect the bite plane when installed in the mouth. Further, the bumper can be made of any material suitable for this use in an orthodontic device.

As used herein, "mesh" refers to a woven or other cross-pattern of filaments, such as wires or threads. When used to form the base of a composite orthodontic device, such a mesh can be made of any material suitable for use in an orthodontic device, and which is capable of being formed into a mesh configuration.

As used herein, "malocclusion" refers to a condition in which the mandibular and maxillary teeth sets experience imperfect contact due to malpositioning. Representative classes of malocclusions are determined based on the relative positions of the first molar in the two arches (upper and lower arches created by each set of teeth) when in occlusion. Type I: normal anteroposterior relationship, but with crowding and rotated teeth. Type II: the lower (mandibular) arch is distal to the upper (maxillary) arch on one or both sides; the lower first molar is distal to the upper first molar. Type II malocclusions often result in an "over jet" situation, where the upper incisors are positioned greater than 1 mm forward of, or anterior to, the lower incisors when the teeth are occluded. Type III: the lower arch is anterior to the upper arch on one or both sides; the lower first molar is anterior to the upper first molar. Type III malocclusions often result in a "negative over jet" situation, where the lower incisors are positioned anterior to the upper incisors when the teeth are occluded.

As used herein, "overbite" refers to a situation in which the upper incisors overlap, or protrude below the cusp of the lower incisors on the facial side thereof, when the teeth are in an occluded position.

As used herein, "bite plane," and "occlusion plane" or "occlusal plane" can be used interchangeably, and refer to a hypothetical plane which is substantially co-extensive with the biting surfaces of the teeth when occlusion of the upper and lower teeth sets occurs. Particularly, such a plane commences at the biting edge of both upper and lower incisors, and extends along the biting surfaces of the teeth in a direction toward the throat.

As used herein, "polymeric resin" refers to any natural or synthetically produced resin, acceptable for use in an orthodontic device. Preferably such a resin, which has been or can be polymerized, or otherwise modified or combined with another substance to take a form which is sufficiently durable to perform the function of the bumper of the device of the present invention, performs the function while at the same time minimizing tooth abrasion and wear. Examples without limitation of substances resulting from a combination with a resin are rubber and plastic.

As used herein, "crumple zone" refers to a cavity or any other structure facilitating deformation in a known or predictable way, which is formed in an orthodontic device, and which is placed at the location for the purpose of facilitating deformation of the device at that location in the specified way when a sufficient amount of force is exerted on the orthodontic device at that specified location during de-bonding of the device.

As used herein, "sharp point" refers to a shape comprising a terminating point which when located on the surface of a bumper and which has been sharpened sufficiently to cause pain or discomfort, provides a deterrent effect when the point is physically contacted by a portion of the patient's anatomy.

As used herein, "sharp ridge" refers to a shape comprising a terminating ridge, or row of points forming a ridge, on the surface of a bumper, which has been sharpened sufficiently to likewise cause a deterrent effect when the ridge, or any terminating point thereof, is physically contacted by the patient.

Figure 5:
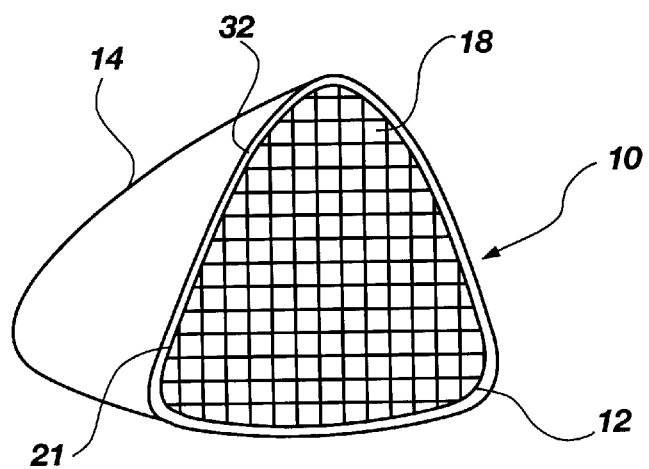
FIG. 5 is a right-rear perspective view of another embodiment of a composite orthodontic device as shown in FIG. 1.

As shown in FIGS. 1 and 5 of the appended drawings, provided for illustration purposes, and not by way of limitation, the invention is embodied in a composite orthodontic device 10. The device has a base 12 configured for facilitating attachment to a tooth surface 13 using an adhesive, and a bumper 14 configured to come in contact with a tooth 15 which vertically opposes the tooth 11 upon which the device is mounted. The bumper is made of a material that does not cause undue abrasion of the opposing tooth because of the contact that occurs between the tooth and the bumper.

Referring now specifically to FIG. 1, the composite orthodontic device 10 is installed upon the lingual surface 13 of an upper incisor 11. In this position, the device impedes the complete occlusion of the maxillary and mandibular sets of teeth. Such an impediment is caused when closing of the teeth is attempted, by contact between a lower portion of the bumper 14 of the device and the biting surface 16 of the lower incisor 15 which vertically opposes the upper incisor upon which the device is installed. The lower portion of the bumper is substantially parallel to a bite plane 23, which appears as a line in FIG. 1. The inability to fully occlude the maxillary and mandibular sets of teeth, and thus to effect an opening of a patient's bite, is instrumental in treating malocclusions as will be appreciated in view of the discussion set out below.

Notably, the device 10 can be installed upon a surface of any tooth necessary to achieve the desired bite-opening result. Device placement can be dictated by a number of factors created by the particular treatment circumstances. For example, in a Type II malocclusion, with an "overbite," where the mandibular set of teeth are excessively posterior to the maxillary set of teeth, the device can be placed on the lingual surface 13 of an upper incisor, or upon the facial surface 17 of a lower incisor. Placement in either position will impede total occlusion of the maxillary and mandibulary sets of teeth and open the bite.

However, when the device 10 is placed in connection with other orthodontic treatment involving brackets (not shown) 19 placed on the facial surface of the teeth, placement of the device on the lingual surface 13 of the upper incisors is necessitated. Conversely, when orthodontic brackets are placed on the lingual surfaces of the teeth, placement of the device on the facial surface 17 of the lower incisors will be required.

In a Type III malocclusion, the mandibular teeth are excessively anterior to the maxillary teeth. In this case, device 10 would be placed upon the lingual surface of a lower incisor 15, or upon the facial surface of an upper incisor 11, as the circumstances dictate, in order to prevent total occlusion of the maxillary and mandibular teeth and achieve the desired bite-opening effect.

In addition to the function of treating malocclusions with a deep bite, the device 10 can be used to treat orally-related compulsive habits, such as thumb sucking and tongue thrusting. When used in such a capacity, the bumper 14 will be configured to provide a tactile deterrent, as more fully described below, and the device will generally be mounted on a lingual surface of a tooth.

Figure 2:
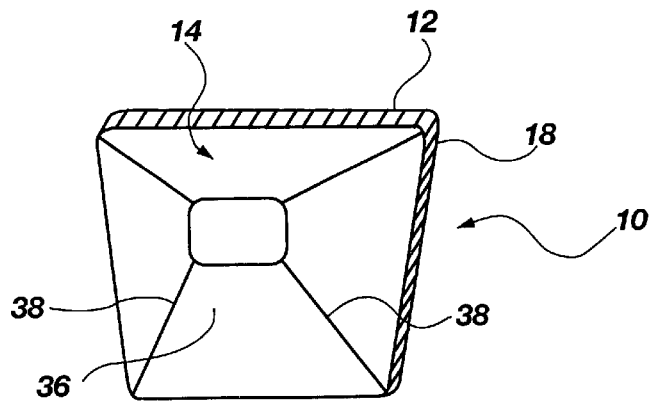
FIG. 2 is a front-top-right perspective view of a composite orthodontic device as shown in FIG. 1.

Referring now to FIG. 2, the bumper 14 is made of a different material than the material of the base 12. While the base can be made of any material suitable for use in an orthodontic device, in one aspect of the invention, the base can comprise a metal.

Metals and other materials which are malleable with a certain degree of elasticity, have been found useful for facilitating attachment and subsequent removal of device 10 to the surface of a tooth when using an adhesive. In particular, because metal is a solid, it is easy to work with, and requires no special handling or time constraints for placement. Further, because of its malleablity and degree of elasticity, it can be deformed to receive a shape which compliments the surface anatomy of a tooth to a certain degree by simply applying it against the tooth surface with a selected degree of pressure. Additionally, a metal base may be easily configured to contain undercuts or other retentive ornamentation which allow the metal base to be cemented against a tooth using minimal amounts of cement while achieving maximum retention. More particularly, the strength of the metal in combination with a retentive surface ornamentation allow for a generically configured base to be used as opposed to a custom fabrication as required by other substances such as acrylic, which must be made to an exacting fit in order to achieve a sufficient bond strength between a tooth and a device. As such, metallic materials can be used in connection with an adhesive and universally installed on a tooth without the need for customization.

Metals useful in device 10 include, but are not limited to: stainless steel, titanium, titanium alloys, brass, gold, silver, and mixtures thereof.

The base 12 of the device 10 can take one of a number of geometric shapes desired or dictated by the particular circumstances of installation, such as circular, oval, trapezoidal, triangular, octagonal, hexagonal, square, or rectangular, for example. In one aspect, the shape of the base can be dictated by the shape of bumper 14. In another aspect a shape having an overall "triangle" aspect and at least a slightly concave shape is desirable because it is stable on an uneven surface, such as a tooth surface. This is because there are three primary contact portions adjacent the three corners at the periphery of the base. The composite device shown in FIG. 5 has a more triangular shaped base 12, but that shown in FIG. 2 approximates a triangle in that the more narrow bottom edge portion acts as one corner and the top two corners complete the triangle.

Figure 3:
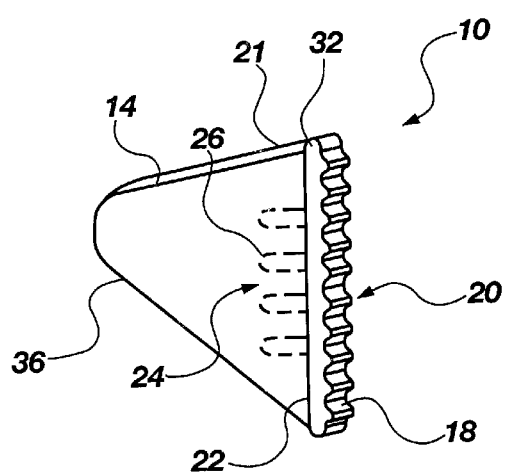
FIG. 3 is a right-rear perspective view of the device shown in FIG. 2.

Referring now to FIGS. 2 and 3, in addition to various shapes, the base 12 can have a surface configuration on both the tooth-contacting surface (i.e. a first surface) 18, and the bumper-contacting surface (i.e. second surface) 22, which facilitates joining of the base with a bumper 14 comprising a second material, such as by use of an adhesive, or by direct adhesion of the bumper material, e.g. a resin. Particularly, by providing surfaces with a roughened or otherwise relieved configuration, a mechanical interlock can be formed with the second material. Generally, the second material is applied to the base in a viscous liquid or semi-solid form, thus allowing the second material to conform to the configuration of the second surface of the base. As such, when the second material is cured and becomes hardened, not only is it bonded to the base "adhesively", but also by interlocking arising from filling in and around irregularities in the second surface which also enhances the strength of the bond.

Referring now particularly to FIG. 3, the first surface 18 of the base 12 is configured to have a plurality of ridges 20 in order to provide mechanical interlocking undercuts and to increase surface area. These are shown enlarged for clarity. In use, an adhesive can be applied to the first surface, or to the surface of a tooth to which the device is to be attached, or to both. The adhesive, being a liquid, viscus liquid, and/or a semi-solid, is able to fill the spaces in between the ridges. Once cured or hardened, the complimentary configuration of the first surface and the hardened adhesive provide mechanical interlocks which enhance the bond between the device and a tooth to which it is attached.

The ridges 20 can run in any direction upon first surface 18, and can be provided in a direction to best resist shear forces from biting for example. The ridges can be disposed in a repeating pattern in order to facilitate uniform bonding strength of the mechanical interlocks. Further, the ridges can have any appropriate shape, such as triangular, square, or circular, spherical, etc., and can be of any height or width which is conducive to enhancing the bonding of the device 10 to a tooth surface.

Figure 6:
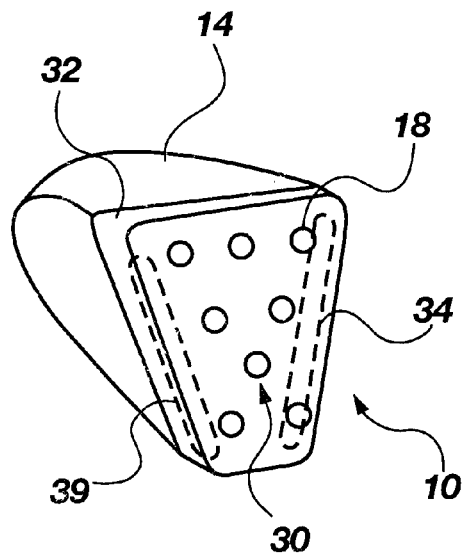
FIG. 6 is a right-top-rear perspective view of another embodiment in accordance with the present invention.

Any of a number of different configurations of the first surface 18 of the base 12 which will facilitate mechanical interlocking. By way of further example, with reference to FIG. 4, in this embodiment a first surface 18 of the base 12 is provided with a plurality of bumps, 28 in order to create the desired mechanical interlock discussed above. It is notable, that the bumps are spherical in shape, but may take any geometric shape as recited above. The base 18 can comprise a mesh, in order to facilitate the mechanical interlock, as illustrated by the embodiment of FIG. 5. FIG. 6 shows an embodiment wherein the first surface 18 of the base 12 is provided with a plurality of cavities 30 in order to facilitate the mechanical interlocks.

Referring again to FIG. 3, the second surface 22 of base 12 is configured to have a plurality of projections 24 which provide a mechanical interlock facilitating a more secure attachment of the bumper 14 to the second surface. Further, the projections may be configured to provide a support for the bumper if needed, or a framework around which the bumper may be built. Alternatively to the plurality of projections, a single projection can be used to achieve a mechanical interlock with the bumper. When a single projection is used, it can be larger than the projections used in plurality.

The projections 24 can be of any of several shapes and sizes desired to facilitate joining of base 12 to bumper 14. By way of example, without limitation, shapes such as elongated rods, hooks 26, ridges, cavities, or bumps can be used. Further, such projections can be organized into repeating patterns, and various shapes can be mixed and matched with other shapes in order to achieve desired results. Thus it is contemplated to be within the scope of the present invention to have, for example, single large or multiple projections in the center of the second surface, surrounded by a plurality of smaller cavities formed on second surface 22. In one embodiment, the second surface comprises a mesh, and in an additional embodiment, both the first 18 and second 22 surfaces comprise a mesh.

The projections 24 of the second surface 22 can form mechanical interlocks in a manner similar to that of the ridges 20 of first surface 18 described above. For example, without limitation, a bumper 14 made of a resin, or other hardenable material, can be molded onto the second surface of the base while in a flowable, malleable, or plastic state, such as a liquid, viscous liquid, or a semi-solid. Once the bumper is molded onto the second surface of the base, it is allowed to cure, or otherwise made or allowed to harden. After the bumper is cured, the complimentary configuration that it received from molding with the second surface provides a mechanical interlock of the bumper with the second surface of the base, thus increasing the strength of the bond therebetween.

With reference to FIGS. 1, 2 and 3, after a course of treatment wherein a composite orthodontic device 10 has been installed is completed, the device must be removed from the tooth 11 to which it is attached. The base 12 of the device can be configured to facilitate acquisition of the device by grasping with a de-bonding tool and deformation of the base in a planned way in order to de-bond the device from a tooth.

Referring to FIGS. 2 and 5, the base 12 can be made of a mesh, which is of a size sufficient to wrap around at least one edge 21 of the bumper 14; thus exposing a portion of the first surface 18 of the base which wraps around the side of the device at the edge 21 when the device is installed on a tooth. The configuration allows for firm acquisition of the base, which facilitates getting purchase on the device with a de-bonding instrument and reduces the difficulty of de-bonding the device. Further, the configuration helps ensure that the bumper will not separate from the base during de-bonding, thus leaving the base attached, or partially attached to the tooth surface.

Referring now to FIG. 3, an edge 32 of the base 12 can have a thickness which is sufficient to provide purchase, and greater thickness allows increased direct contact between the edge of the base and a de-bonding instrument when device is installed on a tooth. Such direct contact facilitates better purchase by the de-bonding instrument and therefore facilitates de-bonding the device 10 from the tooth as mentioned above. However, deformation of the base facilitates de-bonding, and the thickness of the base elsewhere can be minimized to allow it to better "peel" in de-bonding.

Referring now to FIG. 6, in another embodiment the base 12 of the device 10 itself also facilitates the de-bonding of the device from a tooth. In particular, the base can have crumple zones 34 which become deformed when the edges of the base are gripped with a de-bonding tool. The deformation of the crumple zones facilitates the inward movement of edges 32, and upward movement of first surface 18 along the edges thereof, away from a tooth surface. Such movement also greatly facilitates the peeling of the base away from a tooth to which it is bonded.

Turning now to FIG. 2, the bumper 14 of device 10 can be made from a material which is different from the material used to form the base 12 of the device. However, the material optimally should be a material which is softer, or less abrasive, than a tooth enamel, so that when in use, the device does not abrade, wear down, fracture or otherwise damage, or traumatize the surface of the vertically opposing tooth which comes to rest against the bumper. In one embodiment, the bumper can made of a polymeric resin. Resin materials which have been found to be useful include, but are not limited to: acrylic resins, rubber, plastic, microfilled resins, macrofilled resins, unfilled resins, acrylic-metal composites, and mixtures thereof.

The bumper 14 can take one of a number of shapes and/or sizes as required to affect a desired treatment result. For example, without limitation, as shown in FIG. 2, the bumper of device 10 is generally tapered, pyramidal or conically configured with a substantially planar tooth-contacting surface 36 or 36' (depending on which way the device is oriented on the tooth). In one embodiment the tooth contacting surface is angled with respect to base 12, such that the planar surface will be generally parallel to a bite plane (23 in FIG. 1) when installed on a tooth. Further, the edges 38 can be rounded in order to maximize the surface area of the bumper which contacts irregularly positioned teeth, and to prevent stress concentrations at specific points (and attendant tooth wear or damage) from occurring. An orientation parallel to the bite plane can be used when no active proximal or distal movement of the mandible or maxilla is to be initiated in treatment.

Figure 4:
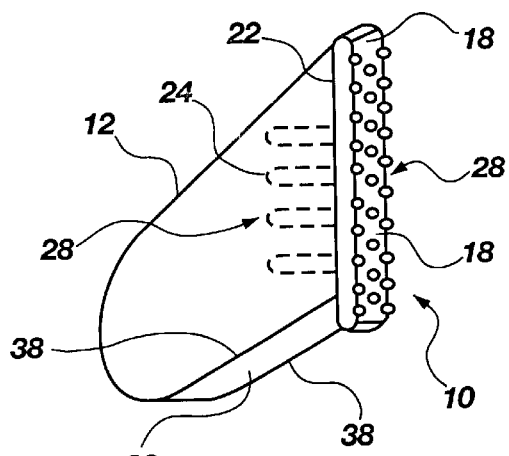
FIG. 4 is a right-bottom-rear perspective view of another embodiment in accordance with the present invention.
Figure 7:
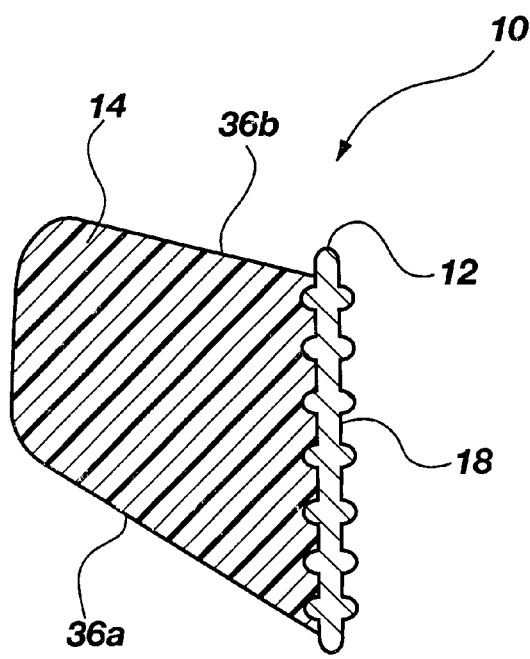
FIG. 7 is a side cross-sectional view of another embodiment in accordance with the present invention.

In contrast, as shown in FIGS. 4 and 7, the bumper 14 can be configured so that the planar tooth-contacting surface 36 or 36' is angled with respect to the bite plane (23 in FIG. 1) when the device 10 is installed on a tooth. Such an intersection initiates either distal or proximal movement of the mandible or maxilla, when the teeth are brought together in an attempt to occlude or bite. The initiation of proximal or distal movement can be thus employed as required in order to achieve a desired guiding or directing effect which ultimately allows the bite to be altered.

Referring now specifically to FIG. 7, the bumper 14 in this embodiment is universally configured to provide a device which has a planar tooth-contacting surface 36a generally parallel to the bite plane when installed in a first orientation and another surface 36b which is disposed so as to intersect with the bite plane at an angle when installed in the mouth. Thus, depending on the desired effect, the device can be mounted so that the substantially planar tooth-contacting surface 36a is generally parallel to the bite plane, or so that surface 36b intersects the bite plane at an angle, simply by reversing the device. Selection of which surface is to interact with the bite plane would, of course, be made depending on the end result desired.

With reference to all the figures, the bumper 14 can be shaped and formed using any suitable method of forming and/or shaping the material(s) from which it is made, as is known in the art, such as vacuum molding, injection molding, casting, etc. Further, the bumper can be joined to base 12 while still in a flowable state, and cured directly onto the base. Conversely, the bumper can be formed, shaped, and cured, and then subsequently joined to the base using adhesives, or other bonding mechanisms known in the art. Further, if desired, the bumper can be further shaped to customize its configurations for treatment of an individual patent, both before and after installation in the mouth due to the relatively softer material being workable after attachment to the base.

Figure 8:
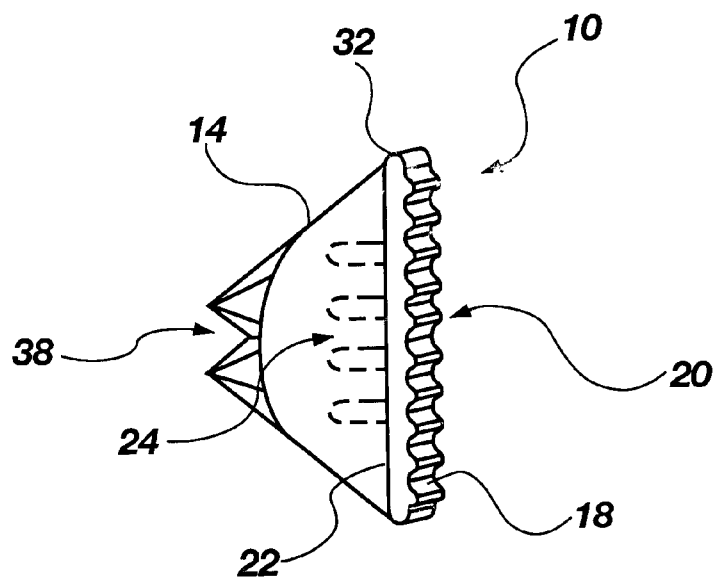
FIG. 8 is a right-rear perspective view of an embodiment configured for treating an orally-related compulsive habit, in accordance with the present invention.
Figure 9:
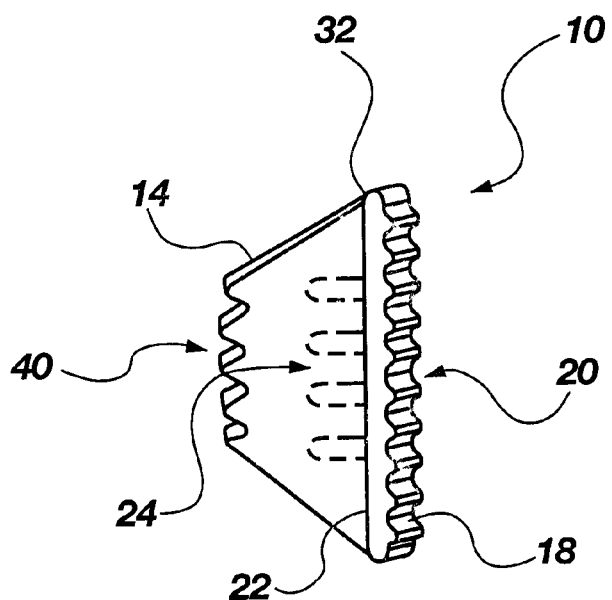
FIG. 9 is a right-rear perspective view of another embodiment of the device shown in FIG. 8.

With reference to FIGS. 8 and 9, in addition to treating malocclusions, the device 10 of the present invention can include a bumper 14 configured to provide a tactile deterrent in order to treat an orally-related compulsive habit, such as tongue thrusting or thumb and digit sucking. One of a number of configurations which provide a tactile deterrent are acceptable. However, by way of example, without limitation, FIGS. 8 and 9 show a composite orthodontic device as described above, having a bumper including a plurality of sharpened points 38, as shown in FIG. 8, or a plurality of sharpened points forming a sharpened ridge 40, as shown in FIG. 9. Other examples of deterrent structures include, but are not limited to, a single sharpened point, a single sharpened ridge, and a bumper of a size which presents sufficient mass to discourage contact.

As will be appreciated, by providing a tactile deterrent, the composite device 10 can effectively break compulsive orally-related habits. In practice, the unpleasant tactile sensation provided by the device is avoided by the patent, and over time the brain becomes trained to avoid the compulsive actions due to the attendant discomfort, and thus the device helps the patient to break the habit without concern of tooth trauma.

With reference to all the drawing figures, it will be appreciated that the present invention provides improved methods of treating malocclusions and orally related compulsive habits. Each method includes attaching a composite device 10 as described above to a tooth, for example an incisor 11. The tooth surface selected for placement is chosen based upon the desired results, and can be either a lingual surface 13, or a facial surface 17.

Further, the method of attaching a bumper 14 of polymeric resin to a tooth can include providing a base 12 as described above, providing a bumper 14 as described above, joining the bumper to the base, and attaching the base to a tooth. The joining can be by curing or molding the bumper in place as described above. In one aspect, the bumper is shaped into a desired shape. Such shaping can be done prior to, or concurrently with, the installment of the device on a tooth.

In another aspect, the present invention provides a method for facilitating removal of a bumper 14 of polymeric resin from a tooth. Such a method includes providing a base 12 as described above. After the device 10 has been installed on a tooth, the device can be more easily de-bonded, due to the configuration of the base, using de-bonding tools such as are known in the art. In another aspect, the method includes providing a crumple zone, or plurality of crumple zones, within the base as describe above.

Of course, it is to be understood that the above-described arrangements are only illustrative of the application of the principles of the present invention. Numerous modifications and alternative arrangements can be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use can be made without departing from the principles and concepts set forth herein.

What is claimed is:

1. A composite orthodontic device, comprising:
   a) a metal base, having a first surface configured for facilitating attachment to a tooth, and a second surface configured to provide a mechanical interlock facilitating joining of a bumper; and
   b) a bumper of a polymeric resin, joined to said base and configured for treating dental malocclusions.

2. A device as set forth in claim 1, wherein said metal is selected from the group consisting of: stainless steel, titanium, titanium alloys, brass, gold, silver, and mixtures thereof.

3. A device as set forth in claim 1, wherein said polymeric resin is selected from the group consisting of: acrylic resins, rubber, plastic, microfilled resins, macrofilled resins, unfilled resins, acrylic-metal composites, and mixtures thereof.

4. A device as set forth in claim 1, wherein the configuration of said first surface comprises a mechanical interlock enhancing attachment to a tooth using an adhesive.

5. A device as set forth in claim 4, wherein the configuration of said first surface comprises a multiplicity of cavities.

6. A device as set forth in claim 5, wherein the multiplicity of cavities are arranged in a repeating pattern.

7. A device as set forth in claim 4, wherein the configuration of said first surface comprises a multiplicity of ridges.

8. A device as set forth in claim 7, wherein the multiplicity of ridges are arranged to form a repeating pattern.

9. A device as set forth in claim 1, wherein the configuration of said second surface comprises a single projection.

10. A device as set forth in claim 9, wherein the single protection comprises a bump.

11. A device as set forth in claim 1, wherein said base has an outer edge configured to facilitate purchase by a de-bonding instrument when installed on a tooth.

12. A device as set forth in claim 11, wherein said base further comprises a crumple zone adjacent to an edge thereof.

13. A device as set forth in claim 12, wherein said base comprises a plurality of said crumple zones.

14. A device as set forth in claim 1, wherein said bumper further comprises a substantially planar tooth-contacting surface which is configured to be disposed generally parallel to a bite plane in the mouth when said device is installed in the mouth.

15. A device as set forth in claim 14, wherein said planar tooth-contacting surface further comprises a rounded edge.

16. A composite orthodontic device, comprising:
   a) a base comprising a first material, having a first surface configured for facilitating attachment to a tooth, and a second surface having a plurality of cavities to provide a mechanical interlock facilitating joining of a bumper comprising a second material different from said first material; and
   b) a bumper comprising said second material, the bumper being joined to said base and configured for treating dental malocclusions.

17. A device as set forth in claim 16, wherein the plurality of cavities are arranged in a repeating pattern.

18. A composite orthodontic device, comprising:
   a) a base comprising a first material, having a first surface configured for facilitating attachment to a tooth, and a second surface having a plurality of projections to provide a mechanical interlock facilitating joining of a bumper comprising a second material different from said first material; and
   b) a bumper comprising said second material, the bumper being joined to said base and configured for treating dental malocclusions.

19. A device as set forth in claim 18, wherein the configuration of the second surface comprises a plurality of ridges.

20. A device as set forth in claim 19, wherein the plurality of ridges are arranged in a repeating pattern.

21. A device as set forth in claim 18, wherein at least one of the plurality of projections comprises a bump.

22. A device as set forth in claim 18, wherein at least one of the plurality of projections comprises a hook.

23. A device as set forth in claim 18, wherein at least one of the plurality of projections further comprises an elongated rod.

24. A composite orthodontic device, comprising:
   a) a base comprising a first material, having a first surface configured for facilitating attachment to a tooth, and a second surface having a single projection comprising an elongated rod, to provide a mechanical interlock facilitating joining of a bumper comprising a second material different from said first material; and b) a bumper comprising said second material, the bumper being joined to said base and configured for treating dental malocclusions.

25. A composite orthodontic device, comprising:

a) a base comprising a first material, having a first surface configured for facilitating attachment to a tooth, and a second surface having a single projection comprising a hook, to provide a mechanical interlock facilitating joining of a bumper comprising a second material different from said first material; and b) a bumper comprising said second material, the bumper being joined to said base and configured for treating dental malocclusions.

26. A composite orthodontic device, comprising:

a) abase comprising a first material, having a first mesh surface for facilitating attachment to a tooth, and a second mesh surface to provide a mechanical interlock facilitating joining of a bumper comprising a second material different from said first material; and b) a bumper comprising said second material, the bumper being joined to said base and configured for treating dental malocclusions.

27. A composite orthodontic device, comprising:

a) a base comprising a first material, having a first surface configured for facilitating attachment to a tooth, and a second surface configured to provide a mechanical interlock facilitating joining of a bumper comprising a second material different from said first material; and b) a bumper comprising said second material, the bumper being joined to said base and configured for treating dental malocclusions, wherein said base has a width greater than a width of said bumper, and wraps around an edge of the bumper, such that a portion of the first surface of the base is exposed when the device is installed on a tooth, for treating dental malocclusions.

28. A composite orthodontic device, comprising:

a) a base comprising a first material, having a first surface configured for facilitating attachment to a tooth, and a second surface configured to provide a mechanical interlock facilitating joining of a bumper comprising a second material different from said first material; and b) a bumper comprising said second material, the bumper being joined to said base, and having a substantially planar tooth-contacting surface with rounded edges and a generally tapering shape, to be disposed generally parallel to a bite plane in the mouth when said device is installed in the mouth, for treating dental malocclusions.

29. A composite orthodontic device, comprising:

a) a base comprising a first material, having a first surface configured for facilitating attachment to a tooth, and a second surface configured to provide a mechanical interlock facilitating joining of a bumper comprising a second material different from said first material; and b) a bumper comprising said second material, being joined to said base and having a substantially planar tooth-contacting surface which intersects a bite plane in the mouth when said device is installed in the mouth at an angle whereby a position of the mandible is shifted with respect to the maxilla as the bumper deflectingly contacts a tooth upon closure of the mouth, for treating dental malocclusions.

30. A device as set forth in claim 29, wherein said planar tooth-contacting surface comprises substantially planar surface with rounded edges.

31. A device as set forth in claim 30, wherein said bumper has a generally tapering shape.

32. A composite orthodontic device comprising:

a) a base made of a first material, having a first surface configured for facilitating attachment to a tooth, and a second surface configured to provide a mechanical interlock for facilitating attachment of a bumper formed of a second material different from said first material; and b) a bumper of a polymeric resin joined to said base, said bumper having a shape configured to provide a deterrent effect when physically contacted upon an outward surface.

33. A device as set forth in claim 32, wherein said first material comprises a metal.

34. A device as set forth in claim 33, wherein said metal is selected from the group consisting of: stainless steel, titanium, titanium alloys, brass, gold, silver, and mixtures thereof.

35. A device as set forth in claim 32, wherein said polymeric resin is selected from the group consisting of: acrylic resins, rubber, plastic, microfilled resins, macrofilled resins, unfilled resins, acrylic-metal composites, and mixtures thereof.

36. A device as set forth in claim 32, wherein the configuration of said first surface comprises a mechanical interlock enhancing attachment to a tooth using an adhesive.

37. A device as set forth in claim 36, wherein the configuration of said first surface comprises a multiplicity of cavities.

38. A device as set forth in claim 37, wherein the multiplicity of cavities are arranged in a repeating pattern.

39. A device as set forth in claim 38, wherein the configuration of said first surface comprises a multiplicity of ridges.

40. A device as set forth in claim 36, wherein the multiplicity of ridges are arranged to form a repeating pattern.

41. A device as set forth in claim 32, wherein the configuration of said second surface comprises a single projection.

42. A device as set forth in claim 41, wherein the single protection comprises a bump.

43. A device as set forth in claim 32, wherein said base has an outer edge configured to facilitate purchase by a de-bonding instrument when installed on a tooth.

44. A device as set forth in claim 43, wherein said base further comprises a crumple zone formed adjacent to an edge thereof.

45. A device as set forth in claim 44, wherein said base comprises a plurality of said crumple zones.

46. A composite orthodontic device comprising:

a) a base made of a first material, having a first surface configured for facilitating attachment to a tooth, and a second surface having a plurality of cavities to provide a mechanical interlock for facilitating attachment of a bumper formed of a second material different from said first material; and b) a bumper joined to said base, said bumper having a shape configured to provide a deterrent effect when physically contacted upon an outward surface.

47. A device as set forth in claim 46, wherein the plurality of cavities are arranged in a repeating pattern.

48. A composite orthodontic device comprising:
a) abase made of a first material, having a first surface configured for facilitating attachment to a tooth, and a second surface having a plurality of projections to provide a mechanical interlock for facilitating attachment of a bumper formed of a second material different from said first material; and
b) a bumper joined to said base, said bumper having a shape configured to provide a deterrent effect when physically contacted upon an outward surface.

49. A device as set forth in claim 48, wherein at least one of the plurality of projections comprises a bump.

50. A device as set forth in claim 48, wherein at least one of the plurality of projections comprises a hook.

51. A device as set forth in claim 48, wherein at least one of the plurality of projections further comprises an elongated rod.

52. A composite orthodontic device comprising:
a) a base made of a first material, having a first surface configured for facilitating attachment to a tooth, and a second surface having a plurality of ridges to provide a mechanical interlock for facilitating attachment of a bumper formed of a second material different from said first material; and
b) a bumper joined to said base, said bumper having a shape configured to provide a deterrent effect when physically contacted upon an outward surface.

53. A device as set forth in claim 52, wherein the plurality of ridges are arranged in a repeating pattern.

54. A composite orthodontic device comprising:
a) a base made of a first material, having a first surface configured for facilitating attachment to a tooth, and a second surface having a single projection comprising an elongated rod, to provide a mechanical interlock for facilitating attachment of a bumper formed of a second material different from said first material; and
b) a bumper joined to said base, said bumper having a shape configured to provide a deterrent effect when physically contacted upon an outward surface.

55. A composite orthodontic device comprising:
a) a base made of a first material, having a first surface configured for facilitating attachment to a tooth, and a second surface having a single projection comprising a hook to provide a mechanical interlock for facilitating attachment of a bumper formed of a second material different from said first material; and
b) a bumper joined to said base, said bumper having a shape configured to provide a deterrent effect when physically contacted upon an outward surface.

56. A composite orthodontic device comprising:
a) a base made of a first material, having a first mesh surface configured for facilitating attachment to a tooth, and a second mesh surface configured to provide a mechanical interlock for facilitating attachment of a bumper formed of a second material different from said first material; and
b) a bumper joined to said base, said bumper having a shape configured to provide a deterrent effect when physically contacted upon an outward surface.

57. A composite orthodontic device comprising:
a) a base made of a first material, having a first surface configured for facilitating attachment to a tooth, and a second surface configured to provide a mechanical interlock for facilitating attachment of a bumper formed of a second material different from said first material; and
b) a bumper joined to said base, said bumper having a shape configured to provide a deterrent effect when physically contacted upon an outward surface, wherein said base has a width greater than a width of said bumper, and wraps around an edge of the bumper, such that a portion of the first surface of the base is exposed when the device is installed on a tooth.

58. A composite orthodontic device comprising:
a) a base made of a first material, having a first surface configured for facilitating attachment to a tooth, and a second surface configured to provide a mechanical interlock for facilitating attachment of a bumper formed of a second material different from said first material; and
b) a bumper joined to said base, said bumper having at least one sharp point to provide a deterrent effect when physically contacted upon an outward surface.

59. A composite orthodontic device comprising:
a) a base made of a first material, having a first surface configured for facilitating attachment to a tooth, and a second surface configured to provide a mechanical interlock for facilitating attachment of a bumper formed of a second material different from said first material; and
b) a bumper joined to said base, said bumper having at least one sharp ridge to provide a deterrent effect when physically contacted upon an outward surface.

60. A composite orthodontic device comprising:
a) a base made of a first material, having a first surface configured for facilitating attachment to a tooth, and a second surface configured to provide a mechanical interlock for facilitating attachment of a bumper formed of a second material different from said first material; and
b) a bumper joined to said base, said bumper having a mass sufficient to act as a deterrent effect when physically contacted upon an outward surface.

61. A method of treating a malocclusion in a human patient comprising the steps of:
a) providing a device comprising a base comprising a first material, having a first surface configured for facilitating attachment to a tooth, and a second surface configured to provide a mechanical interlock facilitating joining of a bumper comprising a second material different from said first material; and
a bumper joined to said base; and attaching said device to a surface of a tooth, within the patient's mouth so as to mitigate the malocclusion.

62. A method as set forth in claim 61, wherein the tooth comprises an incisor.

63. A method as set forth in claim 62, wherein the tooth surface comprises a lingual surface.

64. A method as set forth in claim 62, wherein the surface comprises a facial surface.

65. A method of treating an oral compulsive habit in a human patient, comprising the steps of:
a) providing a device comprising a base comprising a first material, having a first surface configured for facilitating attachment to a tooth, and a second surface configured to provide a mechanical interlock facilitating attachment of a bumper comprising a second material different from said first material; and
a bumper joined to said base, said bumper having a shape configured to provide a deterrent effect on the patient's practice of said habit; and attaching said device to a surface of a tooth so as deter said habit.

66. A method as set forth in claim 65, wherein said compulsive habit comprises thumb sucking.

67. A method as set forth in claim 65, wherein said compulsive habit comprises tongue thrusting.

68. A method of attaching a bumper of polymeric resin to a tooth comprising the steps of:
   a) providing a base comprising a material different from said polymeric resin, and further comprising a first surface configured for facilitating attachment to a tooth, and a second surface configured to provide a mechanical interlock for facilitating attachment of the bumper to the base;
   b) joining the bumper to the second surface of said base; and
   c) attaching the first surface of said base to a tooth.

69. A method as set forth in claim 68, further comprising the step of shaping said bumper into a desired shape.

70. A method as set forth in claim 68, wherein said first and second surfaces comprise a mesh configuration.

71. A method of facilitating removal of a bumper of polymeric resin from a tooth comprising the steps of:
   a) providing a base comprising a malleable material different from said polymeric resin, intermediate the bumper and the tooth the base being configured to facilitate purchase using a de-bonding instrument when the bumper is installed on a tooth;
   b) joining the bumper to a said base; and
   c) joining the base to a tooth.

72. A method as set forth in claim 71, further comprising the step of providing said base with an outer edge having a thickness sufficient to facilitate force-transferring contact by a de-bonding instrument therewith when installed on a tooth.

73. A method as set forth in claim 71, further comprising the step of comprising said base so as to have a width greater than a width of said bumper, and to wrap around an edge of the bumper such that a grasping portion of the base is exposed when the device is installed on on a tooth.

74. A method as set forth in claim 71, further comprising the step of providing a crumple zone within said base adjacent and extending along an edge thereof.

75. A method as set forth in claim 71, further comprising the step of providing a plurality of crumple zones within said base, and extending along a plurality of edges thereof.

* * * * *